US007011916B2

(12) United States Patent
Bender et al.

(10) Patent No.: US 7,011,916 B2
(45) Date of Patent: Mar. 14, 2006

(54) NAPHTHALENE TETRACARBOXYLIC DIIMIDE DIMERS

(75) Inventors: Timothy P. Bender, Port Credit (CA); John F. Graham, Oakville (CA); James M. Duff, Mississauga (CA)

(73) Assignee: Xerox Corporation, Stamford, CT (US)

( * ) Notice: Subject to any disclaimer, the term of this patent is extended or adjusted under 35 U.S.C. 154(b) by 11 days.

(21) Appl. No.: 10/893,637

(22) Filed: Jul. 16, 2004

(65) Prior Publication Data

US 2005/0004365 A1 Jan. 6, 2005

Related U.S. Application Data

(62) Division of application No. 10/197,933, filed on Jul. 17, 2002, now Pat. No. 6,794,102.

(51) Int. Cl.
*G03G 5/047* (2006.01)
*C07D 471/02* (2006.01)

(52) U.S. Cl. ............................ 430/58; 546/66; 546/62; 430/56

(58) Field of Classification Search .................. 546/66, 546/62; 430/58, 56
See application file for complete search history.

(56) References Cited

U.S. PATENT DOCUMENTS

| | | | | |
|---|---|---|---|---|
| 5,343,050 | A * | 8/1994 | Egusa et al. | 257/40 |
| 5,468,583 | A | 11/1995 | Gruenbaum et al. | 430/58 |
| 5,756,744 | A | 5/1998 | Duff et al. | 546/34 |
| 6,794,102 | B1 * | 9/2004 | Bender et al. | 430/56 |

OTHER PUBLICATIONS

Kwan, V.W.S. et al.: Electrochemistry of Langmuir-Blodgett and self-assembled films built from oligomides. Langmuir, vol. 8, pp. 3003-3007, 1992.*

Borsenberger et al., *Organic Photoreceptors for Xerography*, pp. 562-569, 584-587, and 632-633 (1998).

* cited by examiner

*Primary Examiner*—Charanjit S. Aulakh
(74) *Attorney, Agent, or Firm*—Zosan Soong

(57) ABSTRACT

A compound having the Formula I

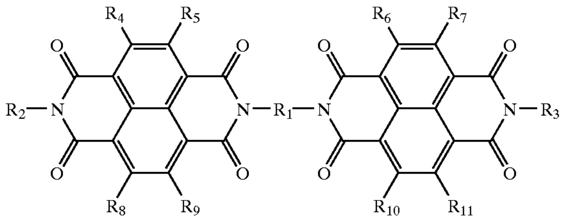

wherein:

$R_1$ is independently selected from the group consisting of a straight chain alkyl group, a branched alkyl group, a cycloalkyl group, an alkoxy group, a monocyclic aromatic group, a polycyclic aromatic group, an alkylaryl group, or an arylalkyl group;

$R_2$ and $R_3$ are independently selected from the group consisting of a straight chain alkyl group, a branched alkyl group, a cycloalkyl group, an alkoxy group, a monocyclic aromatic group, a polycyclic aromatic group, a heterocyclic group, an alkylaryl group, an arylalkyl group, an alkoxyaryl group, an arylalkoxy group, a halogen, and hydrogen;

$R_4$, $R_5$, $R_6$, $R_7$, $R_8$, $R_9$, $R_{10}$ and $R_{11}$ are independently selected from the group consisting of a straight chain alkyl group, a branched alkyl group, a cycloalkyl group, an alkoxy group, a monocyclic aromatic group, a polycyclic aromatic group, an alkylaryl group, an arylalkyl group, an alkoxyaryl group, an arylalkoxy group, an aryloxy group, a halogen, and hydrogen.

8 Claims, 2 Drawing Sheets

Compound 1

NTDI-dimer

NAPHTHALENE TETRACARBOXYLIC DIIMIDE DIMERS

CROSS REFERENCE TO RELATED APPLICATIONS

This application is a divisional application of U.S. application Ser. No. 10/197,933 (filing date Jul. 17, 2002) now U.S. Pat. No. 6,794,102 from which priority is claimed, the disclosure of which is totally incorporated herein by reference.

BACKGROUND OF THE INVENTION

Many electrophotographic elements currently in use are designed to be initially charged with a negative polarity. Such elements contain material which facilitates the migration of positive holes toward the negatively charged surface in imagewise exposed areas in order to cause imagewise discharge. Such material is often referred to as a hole-transport agent. In elements of that type, a positively charged toner material is usually then used to develop the remaining imagewise undischarged areas of negative polarity potential, i.e., the latent image, into a toner image. Because of the wide use of negatively charging elements, considerable numbers and types of positively charging toners have been fashioned and are available for use in electrophotographic developers.

However, for some applications of electrophotography it is more desirable to be able to develop the surface areas of the element that have been imagewise exposed to actinic radiation, rather than those that remain imagewise unexposed. For example, in laser printing of alphanumeric characters it is more desirable to be able to expose the relatively small percentage of surface area that will actually be developed to form visible alphanumeric toner images, rather than waste energy exposing the relatively large percentage of surface area that will constitute undeveloped background portions of the final image. In order to accomplish this while still employing widely available high quality positively charging toners, it is necessary to use an electrophotographic element that is designed to be positively charged. Positive toner can then be used to develop the exposed surface areas, which will have, after exposure and discharge, relatively negative electrostatic potential compared to the unexposed areas, where the initial positive potential will remain. An electrophotographic element designed to be initially positively charged may contain an adequate electron-transport agent, that is, a material which facilitates the migration of photogenerated electrons toward the positively charged insulative element surface.

Electrophotographic elements include both those commonly referred to as single layer or single-active-layer elements and those commonly referred to as multiactive, multilayer, or multi-active-layer elements.

Single-active-layer elements are so named because they contain only one layer that is active both to generate and to transport charges in response to exposure to actinic radiation. Such elements typically comprise at least an electrically conductive layer in electrical contact with an active layer. In single-active-layer elements, the active layer contains a charge-generation material to generate electron/hole pairs in response to actinic radiation and an electron-transport and/or hole-transport agent, which comprises one or more of chemical compounds capable of accepting electrons and/or holes generated by the charge-generation material and transporting them through the layer to effect discharge of the initially uniform electrostatic potential. The active layer is electrically insulative except when exposed to actinic radiation, and it sometimes contains an electrically insulative polymeric film-forming binder, which may itself be the charge-generating material, or it may be an additional material that is not charge-generating. In either case, the transport agent(s) is (are) dissolved or dispersed as uniformly as possible in the layer.

Multiactive elements are so named because they contain at least two active layers, at least one charge generation layer (CGL) which is capable of generating charges, i.e., electron/hole pairs, in response to exposure to actinic radiation, and at least one charge transport layer (CTL) which is capable of accepting and transporting charges generated by the charge-generation layer. Such elements typically comprise at least an electrically conductive layer, a CGL, and a CTL. Either the CGL or the CTL is in electrical contact with both the electrically conductive layer and the remaining CTL or CGL. The CGL contains at least a charge-generation material; the CTL contains at least a charge-transport agent; and either or both layers can contain an electrically insulative film-forming polymeric binder.

In multiactive positively charged photoconductor elements of the type employing at least a CGL and a CTL, the CTL may be the uppermost layer of the element to protect the more mechanically sensitive CGL from wear. Known electron transport agents may suffer from one or more problems upon repeated use, such as high dark decay, insufficient electronic charge transport activity, a gradually increasing residual potential or the like. Certain electron transport agents, such as trinitrofluorenone (TNF), which do exhibit a useful level of sensitivity, suffer from the further disadvantage that they are now suspected to be carcinogens.

Consequently, the art of photoconductor elements continues to seek new electron transport agents which exhibit sufficient sensitivity, but which do not exhibit disadvantages such as above indicated which might restrict their utilization in positively charged photoconductor elements.

Cyclic bis-dicarboximide compounds have previously been proposed for use in photoconductor elements in Gruenbaum et al., U.S. Pat. No. 5,468,583. Electron and bipolar transport are discussed in Borsenberger et al., *Organic Photoreceptors for Xerography, pp.* 562–569, 584–587, and 632–633 (1998).

SUMMARY OF THE DISCLOSURE

The present invention is accomplished in embodiments by providing a compound having the Formula I

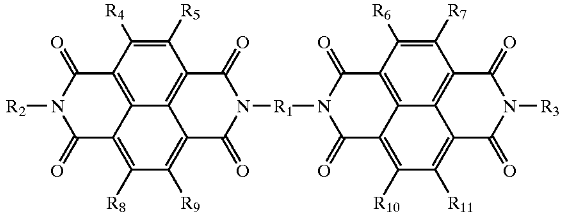

wherein:

$R_1$ is independently selected from the group consisting of a hetero atom containing group and a hydrocarbon group that is optionally substituted at least once with a hetero atom moiety;

$R_2$ and $R_3$ are independently selected from the group consisting of hydrogen, a halogen, a hetero atom containing group and a hydrocarbon group that is optionally substituted at least once with a hetero atom moiety; and $R_4$, $R_5$, $R_6$, $R_7$, $R_8$, $R_9$, $R_{10}$ and $R_{11}$ are independently selected from the group consisting of a nitrogen containing group, a sulfur containing group, a hydroxyl group, a silicon containing group, hydrogen, a halogen, a hetero atom containing group and a hydrocarbon group that is optionally substituted at least once with a hetero atom moiety.

There is also provided in embodiments a compound having the Formula I

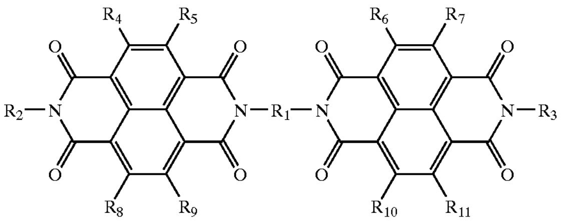

wherein:

$R_1$ is independently selected from the group consisting of a straight chain alkyl group, a branched alkyl group, a cycloalkyl group, an alkoxy group, a monocyclic aromatic group, a polycyclic aromatic group, an alkylaryl group, or an arylalkyl group;

$R_2$ and $R_3$ are independently selected from the group consisting of a straight chain alkyl group, a branched alkyl group, a cycloalkyl group, an alkoxy group, a monocyclic aromatic group, a polycyclic aromatic group, a heterocyclic group, an alkylaryl group, an arylalkyl group, an alkoxyaryl group, an arylalkoxy group, a halogen, and hydrogen;

$R_4$, $R_5$, $R_6$, $R_7$, $R_8$, $R_9$, $R_{10}$ and $R_{11}$ are independently selected from the group consisting of a straight chain alkyl group, a branched alkyl group, a cycloalkyl group, an alkoxy group, a monocyclic aromatic group, a polycyclic aromatic group, an alkylaryl group, an arylalkyl group, an alkoxyaryl group, an arylalkoxy group, an aryloxy group, a halogen, and hydrogen.

BRIEF DESCRIPTION OF THE DRAWINGS

Other aspects of the present invention will become apparent as the following description proceeds and upon reference to the Figures which represent illustrative embodiments.

Unless otherwise noted, the same reference numeral in different Figures refers to the same or similar feature.

DETAILED DESCRIPTION

Figure 1:
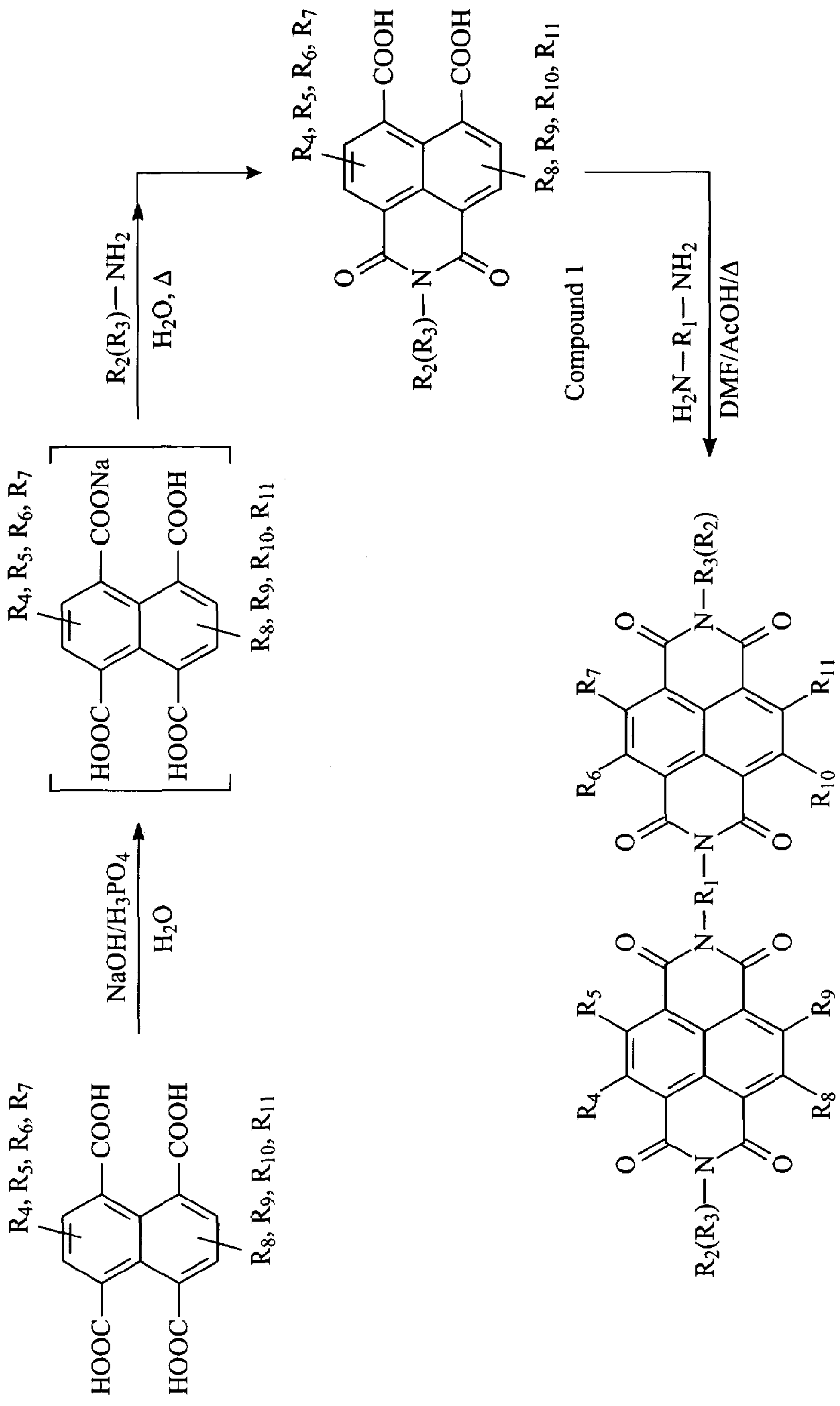
FIG. 1 depicts a first illustrative synthesis route for preparing the present compounds.

The phrase hetero atom containing group indicates that there are present at least one other type of atom other than carbon and hydrogen within the group and that the hetero atom or hetero atoms are part of the main structural chain of the group, for example 3-oxa-pentan-1,5-diyl.

The phrase hetero atom moiety indicates that there are present at least one other type of atom other than carbon and hydrogen within the group and that the hetero atom moiety is not part of the main structural chain of the group, for example 2-hydroxy-propan-1,3-diyl.

The term hydrocarbon refers to any moiety composed of only carbon atoms and hydrogen atoms. The hydrocarbon may be optionally substituted where one or more of the hydrogen atoms is replaced with another substituent. Furthermore, the term hydrocarbon includes for instance acyclic hydrocarbons, alicyclic hydrocarbons, aromatic hydrocarbons and the like which may be optionally substituted.

In embodiments, there is provided a compound of the Formula I

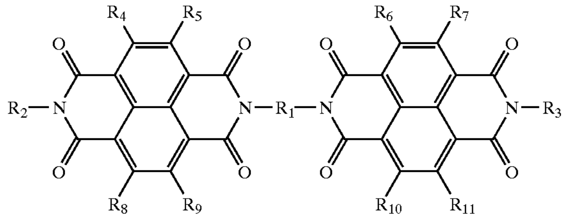

having the following substituents.

A. $R_1$ $R_1$ is independently selected from the group consisting of a hetero atom containing group and a hydrocarbon group that is optionally substituted at least once with a hetero atom moiety.

1. Exemplary Examples of the Hetero Atom Containing Group (for $R_1$)

(a) an alkoxy group having for example 3 to about 30 atoms, particularly 3 to about 6 atoms such as 3-oxa-pentan-1,5-diyl, an aldehyde group, and a ketone group;

(b) a heterocyclic system having for example 11 to about 30 atoms such as N-phenylcarbazol-3,5-diyl; and (c) an alkoxyaryl having for example 7 to about 30 atoms such as 2-methoxybenzen-1,4-diyl and 2-ethoxybenzen-1,4-diyl.

2. Exemplary Examples of the Hydrocarbon Group (for $R_1$)

(a) a straight chain alkyl group having for example 1 to about 30 carbon atoms, particularly 1 to about 6 carbon atoms, such as ethan-1,2-diyl, butan-1,4-diyl and hexan-1,6-diyl;

(b) a branched alkyl group having for example 3 to about 30 carbon atoms, particularly 3 to about 6 carbon atoms such as 2-methylpentan-1,5-diyl and 2,2-dimethylpropan-1,3-diyl;

(c) a cycloalkyl group having for example 3 to about 20 carbon atoms, particularly 4 to about 6 carbon atoms such as cyclopentan-1,3-diyl and cyclohexan-1,4-diyl;

(d) a monocyclic aromatic group such as phenyl like benzen-1,2-diyl, benzen-1,3-diyl and benzen-1,4-diyl;

(e) a polycyclic aromatic group having for example 11 to about 30 carbon atoms such as naphthyl (e.g., naphthalen-1,5-diyl and naphthalene-2,7-diyl) and anthracen-9,10-diyl;

(f) an alkylaryl group having for example 7 to about 30 carbon atoms such as p-xylen-α,α-diyl; and (g) an arylalkyl group having for example 7 to about 30 carbon atoms such as 2,5-diisopropylbenzen-1,4-diyl.

3. Exemplary Examples of Substitutions (for $R_1$)

Any of the hydrocarbon groups can be optionally substituted one, two, or more times with the same or different substituting moiety such as the following:

(a) a nitrogen containing group such as amino and nitro;

(b) a sulfur containing group such as thiol, sulfoxide, sulfate, chlorosulfate;

(c) a hydroxyl group;

(d) a silicon containing group such as a trisubstituted silane where the substituent is a hydrocarbon;

(e) a halogen such as bromine, chlorine, fluorine, and iodine; and (f) a hetero atom moiety, having for example 3 to about 15 atoms, and including an element selected for instance from the group consisting of nitrogen, sulfur, silicon, and oxygen, such as thiophen-2-yl, thiophen-3-yl, pyridin-2-yl, pyridin-3-yl, pyridin-4-yl, furan-2-yl, furan-3-yl and the like.

Exemplary substituted hydrocarbon groups include for instance the following: 3-hydroxyhexan-1,6-diyl; 2-methylbenzen-1,4-diyl; and 2,5-dimethylbenzen-1,4-diyl.

B. $R_2$ and $R_3$ $R_2$ and $R_3$ are independently selected from the group consisting of hydrogen, a halogen (e.g., bromine, chlorine, fluorine, and iodine), a hetero atom containing group and a hydrocarbon group that is optionally substituted at least once with a hetero atom moiety.

1. Exemplary Examples of the Hetero Atom Containing Group (for $R_2$ and $R_3$)

(a) an alkoxy group having for example 3 to about 30 atoms, particularly 3 to about 6 atoms such as 3-oxa-butan-1-yl, 4-methyl-3-oxapent-1-yl, an aldehyde group, and a ketone group;

(b) a heterocyclic system having for example 11 to about 30 atoms such as N-phenylcarbazol-3-yl, thiophen-2-yl, thiophen-3-yl, pyridin-2-yl, pyridin-3-yl, pyridin-4-yl, furan-2-yl, furan-3-yl and the like;

(c) an alkoxyaryl having for example 7 to about 30 atoms such as 4-methoxybenzen-1-yl and 4-ethoxybenzen-1-yl; and (d) an arylalkoxy having for example 7 to about 30 atoms such as 3-oxa-3-phenylpropan-1-yl.

2. Exemplary Examples of the Hydrocarbon Group (for $R_2$ and $R_3$)

(a) a straight chain alkyl group having for example 1 to about 30 carbon atoms, particularly 1 to about 8 carbon atoms, such as ethanyl, butanyl or hexanyl;

(b) a branched alkyl group having for example 3 to about 30 carbon atoms, particularly 3 to about 8 carbon atoms such as 1,2-dimethylpropan-1-yl, 1-methylhexan-1-yl and 1,6-dimethylhexan-1-yl;

(c) a cycloalkyl group having for example 3 to about 20 carbon atoms, particularly 4 to about 6 carbon atoms such as cyclopentanyl and cyclohexanyl;

(d) a monocyclic aromatic group such as phenyl like benzenyl;

(e) a polycyclic aromatic group having for example 11 to about 30 carbon atoms such as naphthyl (e.g., naphthalene-1-yl and naphthalene-2-yl) and anthracen-9-yl;

(f) an alkylaryl group having for example 7 to about 30 carbon atoms such as toluen-α-yl; and (g) an arylalkyl group having for example 7 to about 30 carbon atoms such as 4-ethylbenzen-1-yl and 4-sec-butylbenzen-1-yl.

3. Exemplary Examples of Substitutions (for $R_2$ and $R_3$)

Any of the hydrocarbon groups can be optionally substituted one, two, or more times with the same or different substituting moiety such as the following:

(a) a nitrogen containing group such as amino and nitro;

(b) a sulfur containing group such as thiol, sulfoxide, sulfate, chlorosulfate;

(c) a hydroxyl group;

(d) a silicon containing group such as a trisubstituted silane where the substituent is a hydrocarbon;

(e) a halogen such as bromine, chlorine, fluorine, and iodine; and (f) a hetero atom moiety, having for example 3 to about 15 atoms, and including an element selected for instance from the group consisting of nitrogen, sulfur, silicon, and oxygen, such as thiophen-2-yl, thiophen-3-yl, pyridin-2-yl, pyridin-3-yl, pyridin-4-yl, furan-2-yl, furan-3-yl and the like.

Exemplary substituted hydrocarbon groups include for instance the following: 2-hydroxyethan-1-yl, 3-hydroxypropan-1-yl, 2-methylbenzen-1-yl, 2,6-diisopropylbenzen-1-yl, 2,5-dimethylbenzen-1-yl, 4-methylnapthalen-1-yl, 5-methylnaphthalen-2-yl.

C. $R_4$, $R_5$, $R_6$, $R_7$, $R_8$, $R_9$, $R_{10}$ and $R_{11}$ $R_4$, $R_5$, $R_6$, $R_7$, $R_8$, $R_9$, $R_{10}$ and $R_{11}$ are independently selected from the group consisting of a nitrogen containing group, a sulfur containing group, a hydroxyl group, a silicon containing group, hydrogen, a halogen (e.g., bromine, chlorine, fluorine, and iodine), a hetero atom containing group and a hydrocarbon group that is optionally substituted at least once with a hetero atom moiety.

1. Exemplary Examples of the Hetero Atom Containing Group ($R_4$ Through $R_{11}$)

(a) an alkoxy group having for example 3 to about 30 atoms, particularly 3 to about 6 atoms such as 3-oxa-butan-1-yl, 4-methyl-3-oxapent-1-yl, an aldehyde group, and a ketone group;

(b) a heterocyclic system having for example 11 to about 30 atoms such as N-phenylcarbazol-3-yl, thiophen-2-yl, thiophen-3-yl, pyridin-2-yl, pyridin-3-yl, pyridin-4-yl, furan-2-yl, furan-3-yl and the like;

(c) an alkoxyaryl having for example 7 to about 30 atoms such as 4-methoxybenzen-1-yl and 4-ethoxybenzen-1-yl; and (d) an arylalkoxy having for example 7 to about 30 atoms such as 3-oxa-3-phenylpropan-1-yl.

(e) an aryloxy having for example 7 to about 30 atoms such as 3-methylphenoxy, 4-nonylphenoxy, 1-naphthoxy and 2-naphthoxy.

2. Exemplary Examples of the Hydrocarbon Group ($R_4$ Through $R_{11}$)

(a) a straight chain alkyl group having for example 1 to about 30 carbon atoms, particularly 1 to about 4 carbon atoms, such as ethanyl and butanyl;

(b) a branched alkyl group having for example 3 to about 30 carbon atoms, particularly 3 to about 4 carbon atoms such as 1-methylpropan-1-yl, 1-methylethan-1-yl and 1-methylmethan-1-yl;

(c) a cycloalkyl group having for example 3 to about 20 carbon atoms, particularly 4 to about 6 carbon atoms such as cyclopentanyl and cyclohexanyl;

(d) a monocyclic aromatic group such as phenyl like benzenyl;

(e) a polycyclic aromatic group having for example 11 to about 30 carbon atoms such as naphthyl (e.g., naphthalene-1-yl and naphthalene-2-yl) and anthracen-9-yl;

(f) an alkylaryl group having for example 7 to about 30 carbon atoms such as toluen-α-yl; and (g) an arylalkyl group having for example 7 to about 30 carbon atoms such as 4-ethylbenzen-1-yl and 4-sec-butylbenzen-1-yl.

3. Exemplary Examples of Substitutions on the Hydrocarbon Group and of Substituents for $R_4$, $R_5$, $R_6$, $R_7$, $R_8$, $R_9$, $R_{10}$ and $R_{11}$ The moieties described below are exemplary examples of substitutions on the hydrocarbon group (any of the hydrocarbon groups can be optionally substituted one, two, or more times with the same or different substituting moiety) and of substituents for $R_4$, $R_5$, $R_6$, $R_7$, $R_8$, $R_9$, $R_{10}$ and $R_{11}$.

(a) a nitrogen containing group such as amino and nitro;

(b) a sulfur containing group such as thiol, sulfoxide, sulfate, chlorosulfate;

(c) a hydroxyl group;

(d) a silicon containing group such as a trisubstituted silane where the substituent is a hydrocarbon;

(e) a halogen such as bromine, chlorine, fluorine, and iodine; and (f) a hetero atom moiety, having for example 3 to about 15 atoms, and including an element selected for instance from the group consisting of nitrogen, sulfur, silicon, and oxygen, such as thiophen-2-yl, thiophen-3-yl, pyridin-2-yl, pyridin-3-yl, pyridin-4-yl, furan-2-yl, furan-3-yl and the like.

Exemplary substituted hydrocarbon groups include for instance the following: 2-hydroxyethan-1-yl, 3-hydroxypropan-1-yl, 2-methylbenzen-1-yl, 2,6-diisopropylbenzen-1-yl, 2,5-dimethylbenzen-1-yl, 4-methylnapthalen-1-yl, 5-methylnaphthalen-2-yl.

Figure 2:
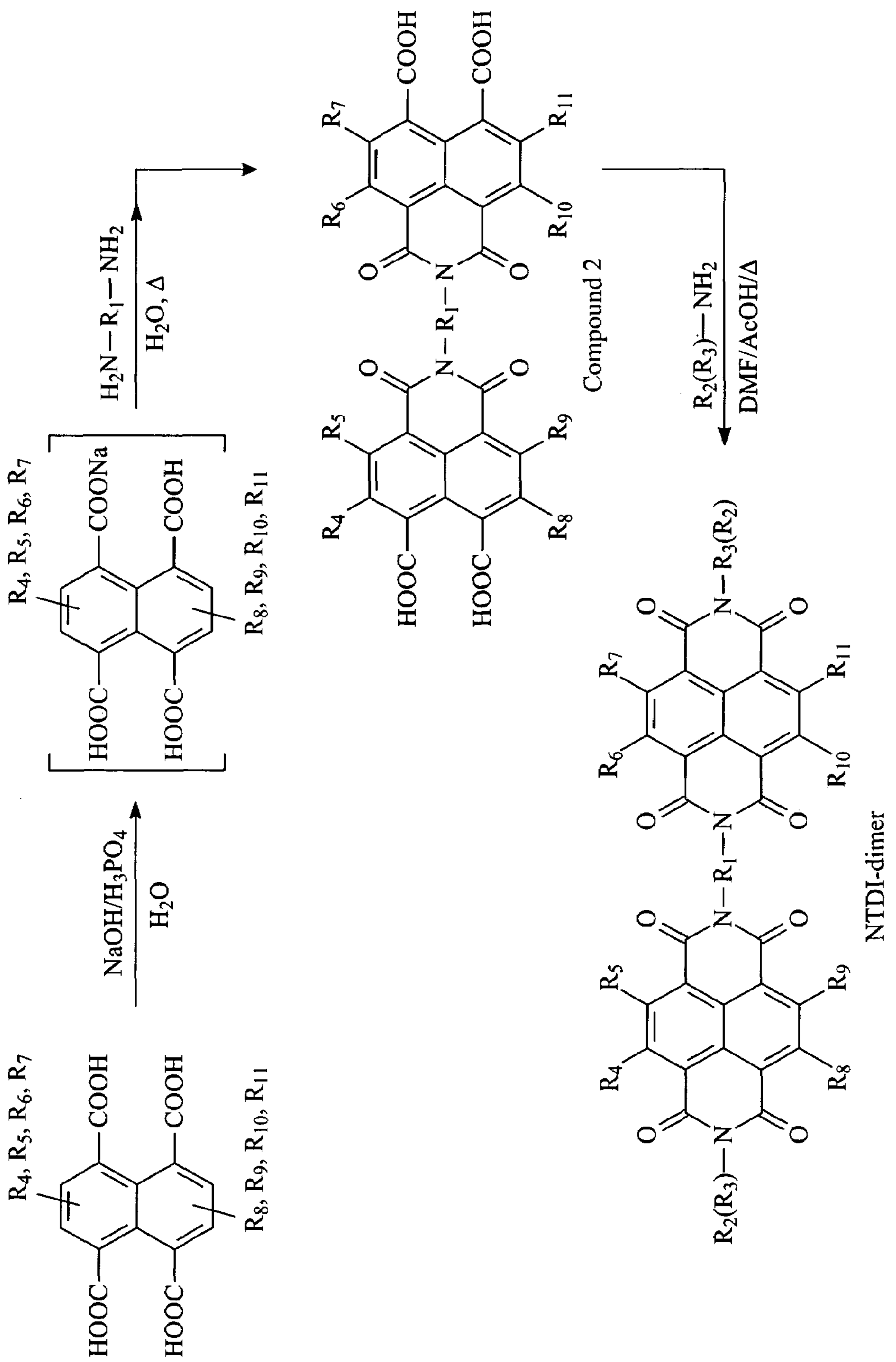
FIG. 2 depicts a second illustrative synthesis route for preparing the present compounds.

FIGS. 1 and 2 depict illustrative synthesis routes to prepare the naphthalene tetracarboxylic diimide dimer ("NTDI-dimer") compounds of the present invention. In FIGS. 1 and 2, $R_2$ and $R_3$ are shown as "$R_2(R_3)$" in the final compound and the reagents because the depicted synthesis pathways are primarily for the situation where $R_2$ and $R_3$ are symmetrical, i.e., they are the same. However, the present disclosure also discusses the preparation of unsymmetrical compounds where $R_2$ and $R_3$ are different from each other.

The synthesis of symmetrical compounds of Formula I (where $R_2$ and $R_3$ are the same) can be accomplished by a multi-step synthesis starting from 1,4,5,8-naphthalenetetracarboxylic acid or dianhydride by either of two routes. In the first route as depicted in FIG. 1, a 1,4,5,8-naphthalene tetracarboxylic diimide dimer is synthesized as follows: 1,4,5,8-naphthalene tetracarboxylic acid or dianhydride is dissolved in aqueous alkali which is then treated sequentially with concentrated phosphoric acid, a monofunctional amine (such as 4-aminobutane or 4-aminopentane) and heated to 90° C. for a period of time. Any insoluble material is filtered after which concentrated phosphoric acid is added to precipitate the product which can be collected, further purified and dried to remove residual water. Reaction of this material with a difunctional amino compound (such as 1,4-diaminobutane or 2,2-dimethyl-1,3-propane diamine) at elevated temperature in a suitable solvent (such as N,N-dimethylformamide, N,N-dimethylacetamide, quinoline, m-cresol, acetic acid and the like and mixtures thereof) yields the title 1,4,5,8-naphthalene tetracarboxylic diimide dimer on isolation and purification.

In the second route as depicted in FIG. 2, a 1,4,5,8-naphthalene tetracarboxylic diimide dimer is synthesized as follows: 1,4,5,8-naphthalene tetracarboxylic acid or dianhydride is dissolved in aqueous alkali which is then treated sequentially with concentrated phosphoric acid, a difunctional amine (such as 1,4-diaminobutane or 2,2-dimethyl-1,3-propane diamine) and heated to 90° C. for a period of time. Any insoluble material is filtered after which concentrated phosphoric acid is added to precipitate the product which can be collected, further purified and dried to remove residual water. Reaction of this material with a monofunctional amino compound (such as 4-aminobutane or 4-aminopentane) at elevated temperature in a suitable solvent (such as N,N-dimethylformamide, N,N-dimethylacetamide, quinoline, m-cresol, acetic acid and the like and mixtures thereof) yields the title 1,4,5,8-naphthalene tetracarboxylic diimide dimer on isolation and purification.

If it is so desired to have a 1,4,5,8-naphthalene tetracarboxylic diimide dimer where R) is not equal to $R_3$ such a dimer could be synthesized as follows: A compound 2 (see FIG. 2) is dissolved in aqueous alkali which is then treated sequentially with concentrated phosphoric acid, a difunctional amine (such as 1,4-diaminobutane or 2,2-dimethyl-1,3-propane diamine) and heated to 90° C. for a period of time. Any insoluble material is filtered after which concentrated phosphoric acid is added to precipitate the product which can be collected, further purified and dried to remove residual water. Reaction of this material with a monofunctional amino compound (such as 4-aminobutane or 4-aminopentane) at elevated temperature in a suitable solvent (such as N,N-dimethylformamide, N,N-dimethylacetamide, quinoline, m-cresol, acetic acid and the like and mixtures thereof) yields the title 1,4,5,8-naphthalene tetracarboxylic diimide dimer on isolation and purification.

It will be apparent to those skilled in the art that the procedures described herein will be generally insensitive to the choice of $R_4$, $R_5$, $R_6$, $R_7$, $R_8$, $R_9$, $R_{10}$ and $R_{11}$. It will also be apparent that the introduction of $R_4$, $R_5$, $R_6$, $R_7$, $R_8$, $R_9$, $R_{10}$ and $R_{11}$ should preferentially be performed before undertaking the synthetic sequence described herein. That is, the starting materials may be changed from 1,4,5,8-naphthalene tetracarboxylic diacid (or dianhydride) to a material that already contains the desired substitution pattern. For those compounds not commercially available their synthesis would be required before undertaking the synthetic procedure described in this invention. The synthesis of naphthalene tetracarboxylic acids is a known process and is illustrated in the following figure (see W. Herbst and K. Hunger, "Industrial Organic Pigments" 2nd edition, VCH, 1997, p. 485):

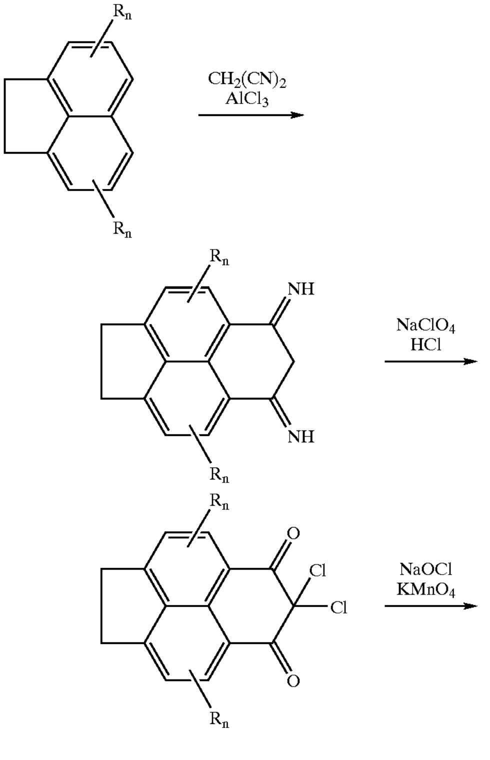

-continued

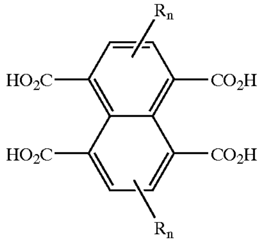

Commercially available acenaphthalene may be successively treated in separate synthetic steps with malononitrile in the presence of aluminum chloride, sodium perchlorate and hydrochloric acid and finally sodium hypochlorite and potassium permanganate. The introduction of a $R_n$ group(s) at any point in the synthesis or by starting the synthetic process from a $R_n$ substituted acenaphthalene would yield a substituted naphthalene tetracarboxylic acid. The use of such a substituted naphthalene tetracarboxylic acid for the synthesis of naphthalene tetrcarboxylic acid diimide dimers as described in this invention would yield compounds substituted in the $R_4$, $R_5$, $R_6$, $R_7$, $R_8$, $R_9$, $R_{10}$ and $R_{11}$ positions of the general structure illustrated in Formula I.

It should also be apparent that for certain choices and combinations of $R_4$, $R_5$, $R_6$, $R_7$, $R_8$, $R_9$, $R_{10}$ and $R_{11}$ the synthetic procedure described herein may yield structural isomers. For example, if 2-chloro-1,4,5,8-naphthalene tetracarboxylic acid was used as a starting material the chloro substituent will end up statistically distributed at the $R_4$, $R_5$, $R_6$, $R_7$, $R_8$, $R_9$, $R_{10}$ and $R_{11}$ positions.

The compounds of Formula I are useful as for example an electron transport agent in electrophotographic elements or other organic electronic devices.

A number of the compounds of Formula I of this invention have a minimum solubility of about 2 g in 100 mL dichloromethane (DCM) and they possess good electron transport capability in photoconductor elements.

The compounds of Formula I are not known to be carcinogenic, are stable under ambient conditions, are readily prepared, and can be compounded for utilization as an electron transport agent since such compounds may be soluble in common organic solvents, especially chlorinated solvents.

For use as an electron transport agent, a compound of Formula I may be dissolved or dispersed together with a preferably dissolved, insulating, film forming binder polymer in a solvent medium, such as a chlorinated hydrocarbon, or the like. This resulting composition can be coated on a surface and then dried to provide the desired charge transport layer.

Naphthalene tetracarboxylic diimide dimers of Formula I may be soluble in embodiments to an extent of at least about 25 weight percent, or to an extent of at least about 40 weight percent, in an organic solvent which is suitable for use as a coating solvent. Exemplary solvents are, for example, tetrahydrofuran, toluene, and halogenated hydrocarbons, such as 1,2-dichloroethane, 1,1,2-trichloroethane, 1,1,2-trichloropropane, 1,1,2,2-tetrachloroethane, dichloromethane, and trichloromethane.

The photoconductor elements of this invention can have any known configuration. The photoconductor elements can have one active layer comprising both a charge generation material and an electron transport agent of Formula I, or they can be multiactive elements. The multiactive elements of this invention have at least one charge generation layer having at least one charge generation material and one charge transport layer having at least one charge transport agent of Formula I. In addition to charge generation layers and charge transport layers, the photoconductor elements of this invention may include electrically conductive layers and optional additional layers, such as subbing layers, adhesive layers, abrasion resistant layers, and electronic charge barrier layers which are all well known in the art.

It is preferred that the photoconductor elements of this invention have dimensional stability. This can be accomplished by using an electrically conductive layer that is itself dimensionally stable, or by forming the element on a dimensionally stable conductive substrate. A dimensionally stable electrically conductive layer or the combination of an electrically conductive layer and a dimensionally stable substrate will be referred to as an electrically conductive support. A dimensionally stable substrate may be thermally stable and may be electrically insulating. Conventional dimensionally stable substrates such as films and sheets of polymeric materials may be used. Examples of polymers used in films include cellulose acetate, polycarbonates, polyesters, such as poly(ethylene terephthalate) and poly (ethylene naphthalate), and polyimides. Typical film substrates have a thickness in the range of about 100 to 200 microns, although thicker and thinner layers can be employed.

The charge transport layer having at least one naphthalene tetracarboxylic diimide dimer of Formula I can be the top layer of the photoconductor element through which the light or activating energy passes to the charge generation layer, because the compounds of Formula I are substantially transparent to visible and near infrared region light. There will be little or no loss in incident light as such light passes through a charge transport layer of this invention. When the charge transport layer is the top layer, it provides the additional benefit of protecting the charge generation layer from abrasion caused when paper, cleaning brushes, or the like, contact the photoconductor element. These photoconductor elements of the invention are particularly useful as positively-charged photoconductor elements.

Photoconductor elements of this invention having a compound of Formula I as the electron transport agent display photosensitivity in the spectral range of for example about 400 to about 900 nm. The exact photosensitivity achieved in any given photoconductor element is dependent upon the choice of charge generation material(s), and the configuration of layer(s) in the photoconductor element. The term "photosensitivity" as used herein means the capacity of a photoconductor element to decrease in surface potential upon exposure to actinic radiation. For purposes of the present invention, photosensitivity is conveniently measured by corona charging the element to a certain potential, exposing the charged element to a monochromatic light and measuring the decrease of the surface potential. The amount of light necessary to discharge the element to a certain potential is defined as the "exposure requirement" for that potential. The exposure requirement to discharge the photoconductor element to half of its initial value is denoted $E_{0.5}$.

The photoconductor elements of this invention can employ various electrically conductive layers. For example, the conductive layer can be a metal foil which is laminated to the substrate. Suitable metal foils include those comprised of aluminum, zinc, copper, and the like. Alternatively, vacuum deposited metal layers upon a substrate are suitable and are presently preferred, such as vapor deposited silver, nickel, gold, aluminum, chromium, and metal alloys. The thickness of a vapor deposited metal layer can be in the range of about 20 to about 500 angstroms. Conductive layers can also comprise a particulate or dissolved organic or inorganic conductor or semiconductor distributed in a binder resin. For example, a conductive layer can comprise compositions of protective inorganic oxide and about 30 to about 70 weight percent of conductive metal particles, such as a vapor deposited conductive cermet layer as described in U.S. Pat. No. 3,880,657. Also see in this connection the teachings of U.S. Pat. No. 3,245,833 relating to conductive layers employed with barrier layers. Organic conductive layers can be employed, such as those comprised of a sodium salt of a carboxyester lactone of maleic anhydride in a vinyl acetate polymer, as taught, for example in U.S. Pat. Nos. 3,007,901 and 3,262,807. The substrate and the conductive layer can also be formulated as a consolidated layer which can be a metal plate or drum. For example, suitable plates or drums can be formed of metals such as aluminum, copper, zinc, brass and steel.

In the photoconductor elements of the invention, the conductive layer is optionally overcoated by a barrier adhesive or subbing layer. The barrier layer typically has a dry thickness in the range of about 0.01 to about 5 microns. Typical subbing layers are solvent soluble, film-forming polymers, such as, for example, cellulose nitrate, nylon, polyesters, copolymers of poly(vinyl pyrrolidone) and vinylacetate, and various vinylidene chloride-containing polymers. Preferred subbing layers are comprised of nylon, and polyacrylic and methacrylic esters. The barrier layer coating composition can also contain minor amounts of various optional additives, such as surfactants, levelers, plasticizers, and the like.

While any convenient method of application of a subbing layer can be used, it is presently preferred to dissolve the polymer in a solvent, and then to coat the solution over the conductive layer.

Preferably, the solvents are volatile, that is evaporable, at temperatures below about 150 degrees C. Examples of suitable solvents include petroleum ethers; aromatic hydrocarbons, such as benzene, toluene, xylene, and mesitylene; ketones, such as acetone, and 2-butanone; ethers, such as tetrahydrofuran and diethyl ether; alkanols, such as isopropyl alcohol; and halogenated aliphatic hydrocarbons, such as methylene chloride, chloroform, and ethylene chloride. Coating solvents include for example chlorinated aliphatic hydrocarbons. A nylon subbing layer may be coated from an alcohol. Mixtures of different solvents or liquids can also be employed.

The barrier layer coating composition is applied by using a technique such as knife coating, spray coating, spin coating, extrusion hopper coating, curtain coating, or the like. After application, the coating composition is conveniently air dried.

In addition to organic polymers, inorganic materials can be utilized for the formation of barrier layers. Silicon dioxide, for example, can be applied to a conductive support by vacuum deposition.

The charge generation layer is applied over the conductive layer, or over the barrier layer, if a barrier layer is employed.

The charge generating (or generation) layer is conveniently comprised of at least one conventional charge generation material that is typically dispersed in a polymeric binder. The layer can have a thickness that varies over a wide range, typical layer thicknesses being in the range of about 0.05 to about 5 microns. As those skilled in the art will appreciate, as layer thickness increases, a greater proportion of incident radiation is absorbed by a layer, but the likelihood increases of trapping a charge carrier which then does not contribute to image formation. Thus, an optimum thickness of a layer can constitute a balance between these competing influences.

Charge generation materials comprise materials that are capable of generating electron/hole pairs upon exposure to actinic radiation in the presence of an electric field and transferring the electrons to an electron-transport agent. The charge generation material is present in a polymeric binder or is present as a separate solid phase. The process by which electron/hole pairs are generated may require the presence of an electron-transport agent. Suitable charge generation materials may be in embodiments substantially incapable of generating and/or transferring electrons/hole pairs to an electron-transport agent in the absence of actinic radiation.

A wide variety of materials known in the art as charge generation materials can be employed including inorganic and organic compounds. Suitable inorganic compounds include, for example, zinc oxide, lead oxide, and selenium. Suitable organic materials include various particulate organic pigment materials, such as phthalocyanine pigments, and a wide variety of soluble organic compounds including metallo-organic and polymeric organic charge generation materials. A partial listing of representative materials may be found, for example, in Research Disclosure, Vol. 109, May, 1973, page 61, in an article entitled "Electrophotographic Elements, Materials and Processes", at paragraph IV(A) thereof. This partial listing of well-known charge generation materials is hereby incorporated by reference.

Examples of suitable organic charge generation materials include phthalocyanine pigments such as a bromoindium phthalocyanine pigment described in U.S. Pat. Nos. 4,666,802 and 4,727,139 or a titanylphthalocyanine pigment such as a titanyl tetrafluoropthalocyanine described in U.S. Pat. No. 4,701,396; various pyrylium dye salts, such as pyrylium, bispyrylium, thiapyrylium, and selenapyrylium dye salts, as disclosed, for example, in U.S. Pat. No. 3,250,615; fluorenes, such as 7,12-dioxo-13-dibenzo(a,h) fluorene, and the like; aromatic nitro compounds of the kind disclosed in U.S. Pat. No. 2,610,120; anthrones such as those disclosed in U.S. Pat. No. 2,670,284; quinones such as those disclosed in U.S. Pat. No. 2,670,286; thiazoles, such as those disclosed in U.S. Pat. No. 3,732,301; various dyes such as cyanine (including carbocyanine), merocyanine, triarylmethane, thiazine, azine, oxazine, xanthene, phthalein, acridine, azo, anthraquinone dyes, and the like, and mixtures thereof.

The charge generation material, or a mixture of charge generation materials, is usually applied from a solution or dispersion in a coating composition to form a charge generating layer in an element over a barrier layer of the type described herein. Also typically present as dissolved solids in a charge generation layer coating composition are a binder polymer and optional additives, such as surfactants, levelers, plasticizers, sensitizers, and the like. The solids comprising a charge generation layer on a 100 weight percent total basis typically comprise 1 to about 70 weight percent of charge-generation material, 0 to about 99 weight percent of polymeric binder, and 0 to about 50 weight percent of total additives. In embodiments, the coating composition contains from about 6 to about 15 weight percent of solids, the balance being solvent. Suitable solvents are those identified above in relation to the barrier layer. In embodiments, additives for a composition to be coated to form a charge generation layer are charge transport agents and surfactants.

Any hydrophobic organic polymer known to the photoconductor element art as a binder can be used for the polymeric binder in the charge generating layer. These polymers are film forming and are preferably organic solvent soluble, and, in solid form, display high dielectric strength and electrical insulating properties. Suitable polymers include, for example, styrene-butadiene copolymers; polyvinyl toluene-styrene copolymers; silicone resins, styrene alkyd resins, silicone-alkyd resins; soya-alkyd resins; poly(vinyl chloride); poly(vinylidene chloride); vinylidene chloride-acrylonitrile copolymers; poly(vinyl acetate); vinyl acetate-vinyl chloride copolymers; poly(vinyl acetate); vinyl acetate-vinyl chloride copolymers; poly(vinyl acetals), such as poly(vinyl butyral); polyacrylic and methacrylic esters, such as poly(methyl methacrylate), poly(n-butyl methacrylate), poly(isobutyl methacrylate), etc.; polystyrene, nitrated polystyrene; polymethylstyrene; isobutylene polymers; polyesters, such as poly[4,4'-(2-norbornylidene)bisphenylene azelate-co-terephthalate(60/40)], and poly[ethylene-co-alkylene-bis(alkylene-oxyaryl)-phenylenedicarboxylate]; phenolformaldehyde resins; ketone resins; polyamides; polycarbonates; polythiocarbonates; poly[ethylene-co-isopropylidene-2,2-bis(ethyleneoxyphenylene) terephthalate]; copolymers of vinyl haloarylates and vinyl acetate, such as poly(vinyl-m-bromobenzoate-co-vinyl acetate); chlorinated polyolefins such as chlorinated polyethylene; and the like. Preferred polymers are polyesters and polycarbonates.

One or more charge transport agents can be added to a charge generation layer coating composition, such as 1,1-bis(4-di-p-tolylaminophenyl)cyclohexane, as taught in U.S. Pat. No. 4,127,412, tri-p-tolylamine, and the like or, electron transport agents, such as compounds of Formula I, or any other electron transport agents known to the art. Coating aids, such as levelers, surfactants, cross linking agents, colorants, plasticizers, and the like, can also be added. The quantity of each of the respective additives present in a coating composition can vary, depending upon results desired and user preferences.

A charge generating layer composition is applied by coating the composition over the barrier layer using a technique such as above described for coating a barrier layer composition. After coating, the charge generating layer composition is usually air dried.

Instead of a charge generation material being dispersed in a polymeric binder, a charge generation layer can, in some cases, depending upon the charge generation material involved, be comprised substantially entirely of only such a material. For example, a perylene dicarboximide pigment of the Formula in column 11, line 45, of U.S. Pat. No. 5,468,583, wherein R is an aryl or arylalkylenyl group, can be applied over an electrically conductive layer under vacuum by sublimination, such as under subatmospheric pressures of about $10^{-2}$ to about $10^{-5}$ mm Hg at temperatures in the range of about 200 degrees C. to about 400 degrees C.

An illustrative charge generation material comprises titanylphthalocyanine or titanyl tetrafluorophthalocyanine pigment described in U.S. Pat. No. 4,701,396 incorporated herein by reference. An illustrative binder in the charge generating layer is poly [4,4'-(2-norbornylidene)bisphenylene azelate-co-terephthalate(60/40)].

The charge transport layer is applied over the charge generation layer. When the charge transport layer contains at least one compound of Formula I, an electron-transporting charge transport layer is produced.

A charge transport layer, if desired, can contain, in addition to at least one compound of Formula I, at least one additional electron transport agent of a type known to the art. Suitable known electron transport agents include 2,4,7-trinitro-9-fluorenone, substituted 4-dicyanomethylene-4H-thiopyran 1,1-dioxides, and substituted anthraquinone biscyanoimines.

In the charge transport layer, the charge transport agent(s) are dispersed, and may be dissolved, in an electrically insulating organic polymeric film forming binder. In general, any of the polymeric binders useful in the photoconductor element art can be used, such as described above for use in a charge generation layer. Additionally, the charge transport layer of this invention can utilize a polymeric binder which itself is a charge transport agent. Examples of such polymeric binders include poly(vinylcarbazole). Exemplary binders include polycarbonates such as bisphenol A polycarbonate, bisphenol Z polycarbonate, and polyesters such as poly[4,4'-(2-norbornylidene)bisphenylene azelate-co-terephthalate(60/40)].

On a 100 weight percent total solids basis, a charge transport layer comprises for example about 10 to 70 weight percent of at least one Formula I compound and about 30 to about 90 weight percent of binder. Typically, a charge transport layer has a thickness in the range of about 10 to about 25 microns, although thicker and thinner layers can be employed.

A charge transport layer of this invention can be produced in a bipolar form, if desired, by additionally incorporating into the layer at least one hole transport agent. Such an agent preferentially accepts and transports positive charges (holes). If employed, the quantity of hole transport agent(s) present in a charge transport layer on a total layer weight basis may be in the range of about 10 to about 50 weight percent, although larger and smaller quantities can be employed.

Examples of suitable organic hole transport agents known to the prior art include:

1. Carbazoles including carbazole, N-ethyl carbazole, N-isopropyl carbazole, N-phenyl carbazole, halogenated carbazoles, various polymeric carbazole materials such as poly(vinyl carbazole), halogenated poly(vinyl carbazole), and the like.
2. Arylamines including monoarylamines, diarylamines, triarylamines and polymeric arylamines. Specific arylamine organic photoconductors include the nonpolymeric triphenylamines illustrated in U.S. Pat. No. 3,180,730; the polymeric triarylamines described in U.S. Pat. No. 3,240,597; the triarylamines having at least one of the aryl radicals substituted by either a vinyl radical or a vinylene radical having at least one active hydrogen-containing group, as described in U.S. Pat. No. 3,567,450; the triarylamines in which at least one of the aryl radicals is substituted by an active hydrogen-containing group, as described by U.S. Pat. No. 3,658,520; and tritolylamine.
3. Polyarylakanes of the type described in U.S. Pat. Nos. 3,274,000; 3,542,547; 3,625,402; and 4,127,412.
4. Strong Lewis bases, such as aromatic compounds, including aromatically unsaturated heterocyclic compounds free from strong electron-withdrawing groups. Examples include tetraphenylpyrene, 1-methylpyrene, perylene, chrysene, anthracene, tetraphene, 2-phenylnaphthalene, azapyrene, fluorene, fluorenone, 1-ethylpyrene, acetyl pyrene, 2,3-benzochrysene, 3,4-benzopyrene, 1,4-bromopyrene, phenylindole, polyvinyl carbazole, polyvinyl pyrene, polyvinyltetracene, polyvinyl perylene and polyvinyl tetraphene.
5. Hydrazones, including the dialkyl-substituted aminobenzaldehyde-(diphenylhydrazones) of U.S. Pat. No. 4,150, 987; alkylhydrazones and arylhydrazones as described in U.S. Pat. Nos. 4,554,231; 4,487,824; 4,481,271; 4,456,671; 4,446,217; and 4,423,129, which are illustrative of the hydrazone hole transport agents.

Other useful hole transport agents are described in Research Disclosure, Vol. 109, May, 1973, pages 61–67 paragraph IV(A)(2) through (13).

One or more other electron transporting agents may be used with the present inventive compounds in photoconductor elements and other electronic devices. Examples of such other electron transporting agents include:

1. A carboxlfluorenone malonitrile (CFM) derivatives represented by the general structure:

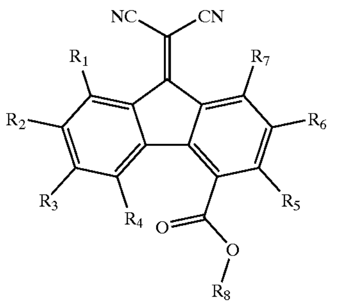

wherein each R is independently selected from the group consisting of hydrogen, alkyl having 1 to 40 carbon atoms, alkoxy having 1 to 40 carbon atoms, phenyl, substituted phenyl, higher aromatic such as naphthalene and anthracene, alkylphenyl having 6 to 40 carbon atoms, alkoxyphenyl having 6 to 40 carbon atoms, aryl having 6 to 30 carbon atoms, substituted aryl having 6 to 30 carbon atoms and halogen.

2. A nitrated fluoreneone derivative represented by the general structure:

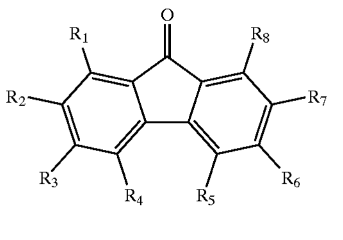

wherein each R is independently selected from the group consisting of hydrogen, alkyl having 1 to 40 carbon atoms, alkoxy having 1 to 40 carbon atoms, phenyl, substituted phenyl, higher aromatic such as naphthalene and anthracene, alkylphenyl having 6 to 40 carbon atoms, alkoxyphenyl having 6 to 40 carbon atoms, aryl having 6 to 30 carbon atoms, substituted aryl having 6 to 30 carbon atoms and halogen, and at least 2 R groups are chosen to be nitro groups.

3. A N,N'bis(dialkyl)-1,4,5,8-naphthalenetetracarboxylic diimide derivative or N,N'bis(diaryl)-1,4,5,8-naphthalenetetracarboxylic diimide derivative represented by the general structure:

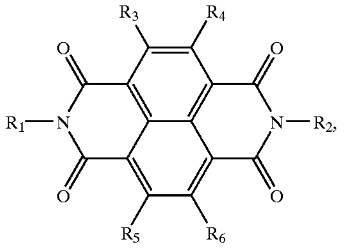

wherein $R_1$ is substituted or unsubstituted alkyl, branched alkyl, cycloalkyl, alkoxy or aryl, such as phenyl, naphthyl, or a higher polycyclic aromatic such as anthracene $R_2$ is alkyl, branched alkyl, cycloalkyl, or aryl, such as phenyl, naphthyl, or a higher polycyclic aromatic such as anthracene or the same as $R_1$; $R_1$ and $R_2$ can be chosen independently to have total carbon number between 1 and 50 but is preferred to be between 1 and 12. $R_3$, $R_4$, $R_5$ and $R_6$ are alkyl, branched alkyl, cycloalkyl, alkoxy or aryl, such as phenyl, naphthyl, or a higher polycyclic aromatic such as anthracene or halogen and the like. $R_3$, $R_4$, $R_5$ and $R_6$ can be the same or different. In the case where $R_3$, $R_4$, $R_5$ and $R_6$ are carbon, they can be chosen independently to have a total carbon number between 1 and 50 but is preferred to be between 1 and 12.

4. A 1,1'-dioxo-2-(aryl)-6-phenyl-4-(dicyanomethylidene) thiopyran derivative represented by the general structure:

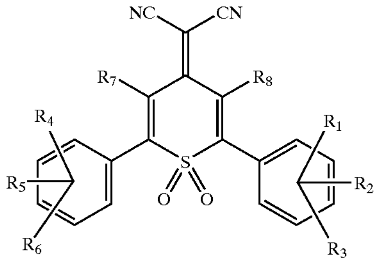

wherein each R is independently selected from the group consisting of hydrogen, alkyl having 1 to 40 carbon atoms, alkoxy having 1 to 40 carbon atoms, phenyl, substituted phenyl, higher aromatic such as naphthalene and anthracene, alkylphenyl having 6 to 40 carbon atoms, alkoxyphenyl having 6 to 40 carbon atoms, aryl having 6 to 30 carbon atoms, substituted aryl having 6 to 30 carbon atoms and halogen.

5. A carboxybenzylnaphthaquinone derivative represented by the following general structure:

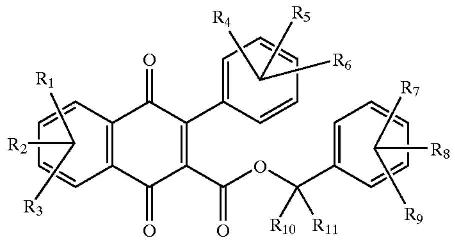

and/or

-continued

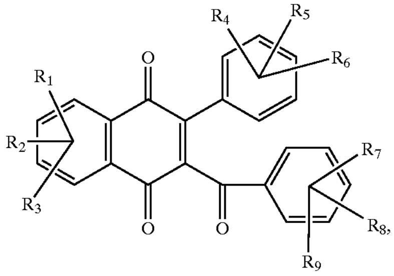

wherein each R is independently selected from the group consisting of hydrogen, alkyl having 1 to 40 carbon atoms, alkoxy having 1 to 40 carbon atoms, phenyl, substituted phenyl, higher aromatic such as naphthalene and anthracene, alkylphenyl having 6 to 40 carbon atoms, alkoxyphenyl having 6 to 40 carbon atoms, aryl having 6 to 30 carbon atoms, substituted aryl having 6 to 30 carbon atoms and halogen.

6. A diphenoquinone represented by the following general structure:

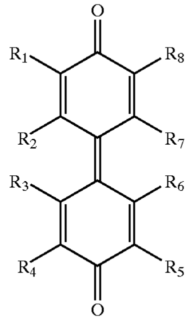

and mixtures thereof, wherein each R is independently selected from the group consisting of hydrogen, alkyl having 1 to 40 carbon atoms, alkoxy having 1 to 40 carbon atoms, phenyl, substituted phenyl, higher aromatic such as naphthalene and anthracene, alkylphenyl having 6 to 40 carbon atoms, alkoxyphenyl having 6 to 40 carbon atoms, aryl having 6 to 30 carbon atoms, substituted aryl having 6 to 30 carbon atoms and halogen.

In addition to an electron transport agent of Formula I, and optionally additional charge transport agent(s) and a binder polymer, the charge transport layers in the photoconductor elements of this invention may contain various optional additives, such as surfactants, levelers, plasticizers, and the like. On a 100 weight percent total solids basis, a charge transport layer can contain for example up to about 15 weight percent of such additives, although it may contain less than about 1 weight percent of such additives.

In embodiments, the charge transport layer solid components are conveniently preliminarily dissolved in a solvent to produce a charge transport layer composition containing for example about 8 to about 20 weight percent solids with the balance up to 100 weight percent being the solvent. The solvents used can be those hereinabove described.

Coating of the charge-transport layer composition over the charge generation layer can be accomplished using a solution coating technique such as knife coating, spray coating, spin coating, extrusion hopper coating, curtain coating, and the like. After coating, the charge transport layer composition is usually air dried.

A charge transport layer can be formed of two or more successive layers each of which has the same or different total solids composition. In such event at least one charge transport sublayer contains at least one compound of Formula I.

Photoconductor elements of this invention may display dark decay values of for example no more than about 20 V/sec, or no more than about 5 V/sec. The term "dark decay" as used herein means the loss of electric charge and consequently, electrostatic surface potential from a charged photoconductor element in the absence of activating radiation.

For present purposes of measuring dark decay, a single-active-layer photoconductive element or a multilayered photoconductor element is charged by use of a corona discharge device to a surface potential in the range of about +300 to about +600 volts. Thereafter, the rate of charge dissipation and decrease of surface potential in volts per second is measured. The element is preliminarily dark adapted and maintained in the dark without activating radiation during the evaluation using ambient conditions of temperature and pressure.

Preferred photoconductor elements of this invention display reusability, that is, the ability to undergo repeated cycles of charging and discharging without substantial alteration of their electrical properties.

Those skilled in the art will appreciate that other variations in the structure of photoconductor elements incorporating a compound of Formula I are possible and practical. For example, various different layer arrangements can be employed. Thus, a transport layer can be positioned between two charge generation layers which can have the same or different respective compositions and layer thicknesses. Also, a charge generation layer can be positioned between two charge-transport layers only one of which may contain a compound of Formula I.

The invention will now be described in detail with respect to specific embodiments thereof, it being understood that these examples are intended to be illustrative only and the invention is not intended to be limited to the materials, conditions, or process parameters recited herein. All percentages and parts are by weight unless otherwise indicated.

Compounds of the type illustrated in Formula I can be prepared according to the general schemes shown in FIGS. 1–2 with the preferred route established empirically to be the route depicted in FIG. 2. This route is preferred since the intermediate compound 2 (see Example 1 below) can be prepared at higher purity levels than a compound 1 (see Example 2 below). These examples are meant as an illustration and those skilled in the art of organic synthesis will understand that there may be other means of synthesizing compounds of this type.

EXAMPLE 1

Synthesis of a Compound 2 Using Route Depicted in FIG. 2 where $R_1$ is 2-methylpentan-1,5-diyl and $R_4$, $R_5$, $R_6$, $R_7$, $R_8$, $R_9$, $R_{10}$ and $R_{11}$ are Hydrogen To 1.2 L of distilled deionized water sodium hydroxide (64 g, ACS reagent) was dissolved. To this, 1,4,5,8-naphthalene tetracarboxylic acid (121.6 g) was dissolved and any insoluble materials were filtered. Concentrated phosphoric acid (46.1 g, ACS reagent) was added and the resulting mixture heated to 90° C. for ½ hour then cooled to 50° C. at which time 2-methyl-1,5-pentanediamine (23.7 g, commercially available as Dytek A diamine from DuPont) was added and the solution heated at 90° C. for 5 hours then cooled to room temperature. Any insoluble materials were filtered (typically 5 g) and the solution was acidified with concentrated phosphoric acid (70 mL, ACS reagent). The precipitated materials were filtered and redissolved in 1.2 L distilled deionized water containing potassium hydroxide (60 g, ACS reagent). Any insoluble materials were filtered and the resulting solution was acidified with concentrated phosphoric acid (60 mL, ACS reagent). The resulting precipitate was isolated and freeze dried for 3 days. The yield was 185 g. The structure and purity of the material could be confirmed using $^1$H NMR in DMSO-$d_6$ solvent. The material was found to be better than 99% pure (based on moles). In the case of the use of 1,3-diaminopropane instead of 2-methyl-1,5-diaminopentane the yield was 87 g. In the case of the use of 2,2-dimethyl-1,3-diaminopropane instead of 2-methyl-1,5-diaminopentane the yield was 130 g.

EXAMPLE 2

Synthesis of a Compound 1 Using the Route Depicted in FIG. 1 where $R_2$ and $R_3$ are pentan-1-yl and $R_4$, $R_5$, $R_6$, $R_7$, $R_8$, $R_9$, $R_{10}$ and $R_{11}$ are Hydrogen To 1.2 L of distilled deionized water sodium hydroxide (64 g, ACS reagent) was dissolved. To this, 1,4,5,8-naphthalene tetracarboxylic acid (121.6 g) was dissolved and any insoluble materials were filtered. Concentrated phosphoric acid (46.1 g, ACS reagent) was added and the resulting mixture heated to 90° C. for ½ hour then cooled to 50° C. at which time 1-aminopentane (50 g) was added and the solution heated at 90° C. for 5 hours then cooled to room temperature. Any insoluble materials were filtered (typically 5 g) and the solution was acidified with concentrated phosphoric acid (70 mL, ACS reagent). The precipitated materials were filtered and redissolved in 1.2 L distilled deionized water containing potassium hydroxide (60 g, ACS reagent). Any insoluble materials were filtered and the resulting solution was acidified with concentrated phosphoric acid (60 mL, ACS reagent). The resulting precipitate was isolated and freeze dried for 3 days. Yield was typically 95 g. The structure and purity of the material could be confirmed using $^1$H NMR in DMSO-$d_6$ solvent. This material is typically between 60–90% desired compound (based on moles) and between 40–10% (based on moles) 1,4,5,8-naphthalene tetracarboxylic acid depending on the structure of the amine used. In the case of 1-aminopentane the material was 90% the desired compound and 10% 1,4,5,8-naphthalene tetracarboxylic acid.

EXAMPLE 3

Synthesis of a NTDI-Dimer From a Compound 2 Using the Route Depicted in FIG. 2 where $R_1$ is 2-methylpentan-1,5-diyl, $R_2$ and $R_3$ are 1-methylhexan-1-yl and $R_4$, $R_5$, $R_6$, $R_7$, $R_8$, $R_9$, $R_{10}$ and $R_{11}$ are Hydrogen A compound 2 where $R_1$ is 2-methylpentan-1,5-diyl (13 g) is heated in a mixture of N,N-dimethylformamide (175 mL) and acetic acid (25 mL) along with 2-aminoheptane (7 mL) for 2 hours at reflux. Any insoluble materials are filtered while still hot and the resulting filtrate cooled to room temperature (25° C.) and diluted to 400 mL with methanol. Addition of 500 mL of distilled deionized water is nessasary to affect precipitation. The precipitate is collected and boiled twice in methanol (150 mL) for 30 minutes. The material is collected and dried at 60° C. and 10 mmHg overnight. The purity and identity of the compound is confirmed by $^1$H NMR in chloroform-d.

EXAMPLE 4

Device Fabrication and Testing

A pigment dispersion was prepared by roll milling 2.15 gm Type V hydroxygallium phthalocyanine pigment particles and 2.15 gm poly(4,4'-diphenyl-1,1'-cyclohexane carbonate) binder (PCZ400, available from Mitsubishi Gas Chemical Co., Inc.) in 26.5 gm methylene chloride ($CH_2Cl_2$) and 6.6 gm monochlorobenzene with 280 grams of 3 mm diameter steel balls for ~25–30 hours.

Separately, 1.86 gm poly(4,4'-diphenyl-1,1'-cyclohexane carbonate) was weighed along with 1.22 gm N,N'-diphenyl-N,N'-bis(methylphenyl)-1,1-biphenyl-4,4'-diamine, 0.61 gm N,N'bis(1,2-dimethylpropyl)-1,4,5,8-naphthalenetetracarboxylic diimide, 0.2 gm 2,2-dimethylpropyl-2-heptyl dimer and 8.76 gm methylene chloride and 2.19 gm monochlorobenzene. This mixture was rolled in a glass bottle until the solids were dissolved, then 1.41 gm of the above pigment dispersion was added to form a dispersion containing Type V hydroxy gallium phthalocyanine, poly(4,4'-diphenyl-1,1'-cyclohexane carbonate), N,N'-diphenyl-N,N'-bis(methylphenyl)-1,1-biphenyl-4,4'-diamine, N,N'bis(1,2-dimethylpropyl)-1,4,5,8-naphthalenetetracarboxylic diimide and 2,2-dimethylpropyl-2-heptyl dimer in a solids weight ratio of (2:48:30:15:5) and a total solid contents of 27 percent; and rolled to mix (without milling beads). Various dispersions were prepared at total solids contents ranging from 25 percent to 28.5 percent. The dispersions were applied with a 6 mil film coating applicator to an aluminized MYLAR® (plolyethylene terephthlalate) and dried at 115° C. for 60 minutes to result in a thickness for the layer of about 18 microns. The thickness of the resulting dried layers was determined by capacitive measurements and a thickness gauge.

The xerographic electrical properties of the above prepared photoconductive imaging member can be determined by known means, including electrostatically charging the surfaces thereof with a corona discharge source until the surface potentials, as measured by a capacitively coupled probe attached to an electrometer, attained an initial value Vo of about +600 volts. After resting for 0.5 second in the dark, the charged members attained a surface potential of Vddp, dark development potential. Each member was then exposed to light from a filtered Xenon lamp thereby inducing a photodischarge which resulted in a reduction of surface potential to a Vbg value, background potential. The percent of photodischarge was calculated as 100×(Vddp−Vbg)/Vddp. The desired wavelength and energy of the exposed light was determined by the type of filters placed in front of the lamp. The monochromatic light photosensitivity was determined using a narrow band-pass filter. The photosensitivity of the imaging member is usually provided in terms of the amount of exposure energy in ergs/cm$^2$, designated as $E_{1/2}$, required to achieve 50 percent photodischarge from Vddp to half of its initial value. The higher the photosensitivity, the smaller is the $E_{1/2}$ value. The $E_{7/8}$ value corresponds to the exposure energy required to achieve ⅞ photodischarge from Vddp. The device was finally exposed to an erase lamp of appropriate light intensity and any residual potential (Vresidual) was measured. The imaging member was tested with an monochromatic light exposure at a wavelength of 780+/−10 nanometers and an erase light with the wavelength of 600 to 800 nanometers and intensity of 150 ergs.cm$^2$. Photoinduced discharge characteristics (PIDC) curves in positive charging mode of a 18.4 micrometer thick device exhibited an $E_{1/2}$ of 2.2 ergs/cm$^2$, an $E_{7/8}$ of 8.6 ergs/cm$^2$ and a residual potential of approximately 30 volts.

The invention claimed is:

1. A photoconductor element comprising: a charge generation material and an electron transport agent, wherein the electron transport agent includes a compound having the Formula I

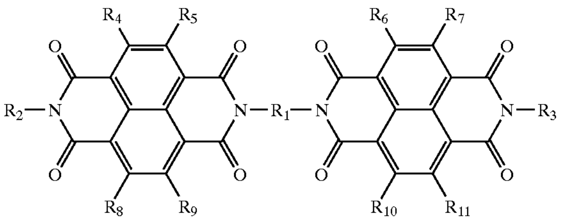

wherein:

$R_1$ is independently selected from the group consisting of a straight chain alkyl group, a branched alkyl group, a cycloalkyl group, an alkoxy group;

$R_2$ and $R_3$ are independently selected from the group consisting of a straight chain alkyl group, a branched alkyl group, a cycloalkyl group, an alkoxy group, a monocyclic aromatic group, a polycyclic aromatic group, a heterocyclic group, an alkylaryl group, an arylalkyl group, an alkoxyaryl group, an arylalkoxy group, a halogen, and hydrogen;

$R_4$, $R_5$, $R_6$, $R_7$, $R_8$, $R_9$, $R_{10}$ and $R_{11}$ are independently selected from the group consisting of a straight chain alkyl group, a branched alkyl group, a cycloalkyl group, an alkoxy group, a monocyclic aromatic group, a polycyclic aromatic group, an alkylaryl group, an arylalkyl group, an alkoxyaryl group, an arylalkoxy group, an aryloxy group, a halogen, and hydrogen.

2. The photoconductor element of claim 1 wherein: $R_4$, $R_5$, $R_6$, $R_7$, $R_8$, $R_9$, $R_{10}$, and $R_{11}$ are hydrogen.

3. The photoconductor element of claim 1 wherein:

$R_2$ and $R_3$ are the same; and $R_4$, $R_5$, $R_6$, $R_7$, $R_8$, $R_9$, $R_{10}$, and $R_{11}$ are hydrogen.

4. The photoconductor element of claim 1 wherein:

$R_2$ and $R_3$ are the same; and $R_4$, $R_5$, $R_6$, $R_7$, $R_8$, $R_9$, $R_{10}$, and $R_{11}$ are the same but different from $R_9$ and $R_3$.

5. A photoconductor element comprising:

an electrically conductive layer;

a layer comprising a binder, a charge generation material, and an electron transport agent including a compound having the Formula I

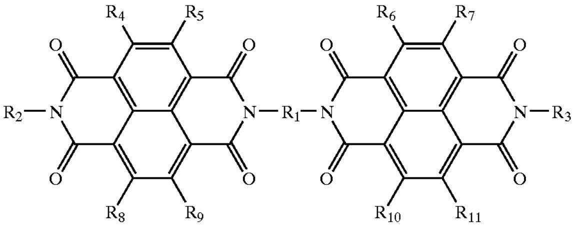

wherein:

$R_1$ is independently selected from the group consisting of a straight chain alkyl group, a branched alkyl group, a cycloalkyl group, an alkoxy group;

$R_2$ and $R_3$ are independently selected from the group consisting of a straight chain alkyl group, a branched alkyl group, a cycloalkyl group, an alkoxy group, a monocyclic aromatic group, a polycyclic aromatic group, a heterocyclic group, an alkylaryl group, an aiylalkyl group, an alkoxyaryl group, an arylalkoxy group, a halogen, and hydrogen;

$R_4$, $R_5$, $R_6$, $R_7$, $R_8$, $R_9$, $R_{10}$ and $R_{11}$ are independently selected from the group consisting of a straight chain alkyl group, a branched alkyl group, a cycloalkyl group, an alkoxy group, a monocyclic aromatic group, a polycyclic aromatic group, an alkylaryl group, an arylalkyl group, an alkoxyaryl group, an arylalkoxy group, an aryloxy group, a halogen, and hydrogen.

6. The photoconductor element of claim 5 wherein:

$R_1$, $R_5$, $R_6$, $R_7$, $R_8$, $R_9$, $R_{10}$, and $R_{11}$ are hydrogen.

7. The photoconductor element of claim 5 wherein:

$R_2$ and $R_3$ are the same; and $R_4$, $R_5$, $R_6$, $R_7$, $R_8$, $R_9$, $R_{10}$, and $R_{11}$ are hydrogen.

8. The photoconductor element of claim 5 wherein:

$R_2$ and $R_3$ are the same; and $R_4$, $R_5$, $R_6$, $R_7$, $R_8$, $R_9$, $R_{10}$, and $R_{11}$ are the same but different from $R_2$ and $R_3$.

* * * * *